United States Patent [19]

Okabayashi et al.

[11] Patent Number: 5,643,792

[45] Date of Patent: Jul. 1, 1997

[54] **MUTANT STRAIN OF *PICHIA PASTORIS* WHICH UTILIZES METHANOL IN THE PRESENCE OF GLUCOSE**

[75] Inventors: Ken Okabayashi; Takao Ohmura; Kazumasa Yokoyama, all of Hirakata; Haruhide Kawabe, Osaka, all of Japan

[73] Assignee: The Green Cross Corporation, Osaka, Japan

[21] Appl. No.: 181,242

[22] Filed: Jan. 13, 1994

[30] Foreign Application Priority Data

Jan. 13, 1993 [JP] Japan ................. 5-004289

[51] Int. Cl.$^6$ ................. C12N 1/15; C12N 15/11
[52] U.S. Cl. ................. 435/254.23; 536/24.1
[58] Field of Search ................. 435/252.1, 252.3, 435/255.5, 254.23, 254.22, 255.4, 255.6, 69.1, 69.2, 69.51, 69.6, 71.1, 71.2; 536/24.1

[56] References Cited

FOREIGN PATENT DOCUMENTS

| 0226846 | 7/1987 | European Pat. Off. ......... C12N 15/00 |
| 0244598 | 11/1987 | European Pat. Off. ......... C12N 15/00 |
| 0344459 | 4/1989 | European Pat. Off. ......... C12N 15/00 |
| 0374282 | 6/1990 | European Pat. Off. ......... C12N 15/78 |
| 0506040 | 9/1992 | European Pat. Off. ......... C12N 15/81 |
| WO92/04441 | 3/1992 | WIPO ......... C12N 9/36 |

OTHER PUBLICATIONS

Waleh et al., *Gene*, 117: 7–14 (1992).
Warnes et al., *Biotech & Bioengineering*, 38:1050–1058 (1991).
Titorenko et al., *Genetika*, 27(5):791–800 (1991).
Database Biotech Abstract Neale et al., *Appl. Mol. Genet. Fungi*, 1991, pp. 118–128.
Abstract Pap. Am. Chem. Soc., Jain et al., vol. 194th, 30 Aug. 1987, No. 34.
Database Biotech. Abstr., Janowicz et al., *Eur. Conf. Biotechnol.*, pp. 82–83.
Sakai et al., *App. Environ. Microbiol.*, vol. 53, No. 8, 1987, pp. 1812–1818.

*Primary Examiner*—James S. Ketter
*Attorney, Agent, or Firm*—Sughrue, Mion, Zinn, Macpeak & Seas

[57] ABSTRACT

A methylotrophic and glucotrophic mutant strain capable of producing a heterologous protein and a method for producing a heterologous protein, comprising culture of the mutant strain. The mutant strain of the present invention can be grown in a medium containing both methanol and glucose, with the effect that the growth of the strain and production of a heterologous protein proceed at the same time. Accordingly, a heterologous protein can be produced in a large amount in a short time.

10 Claims, 5 Drawing Sheets

GTS115

GCP104

GCP101

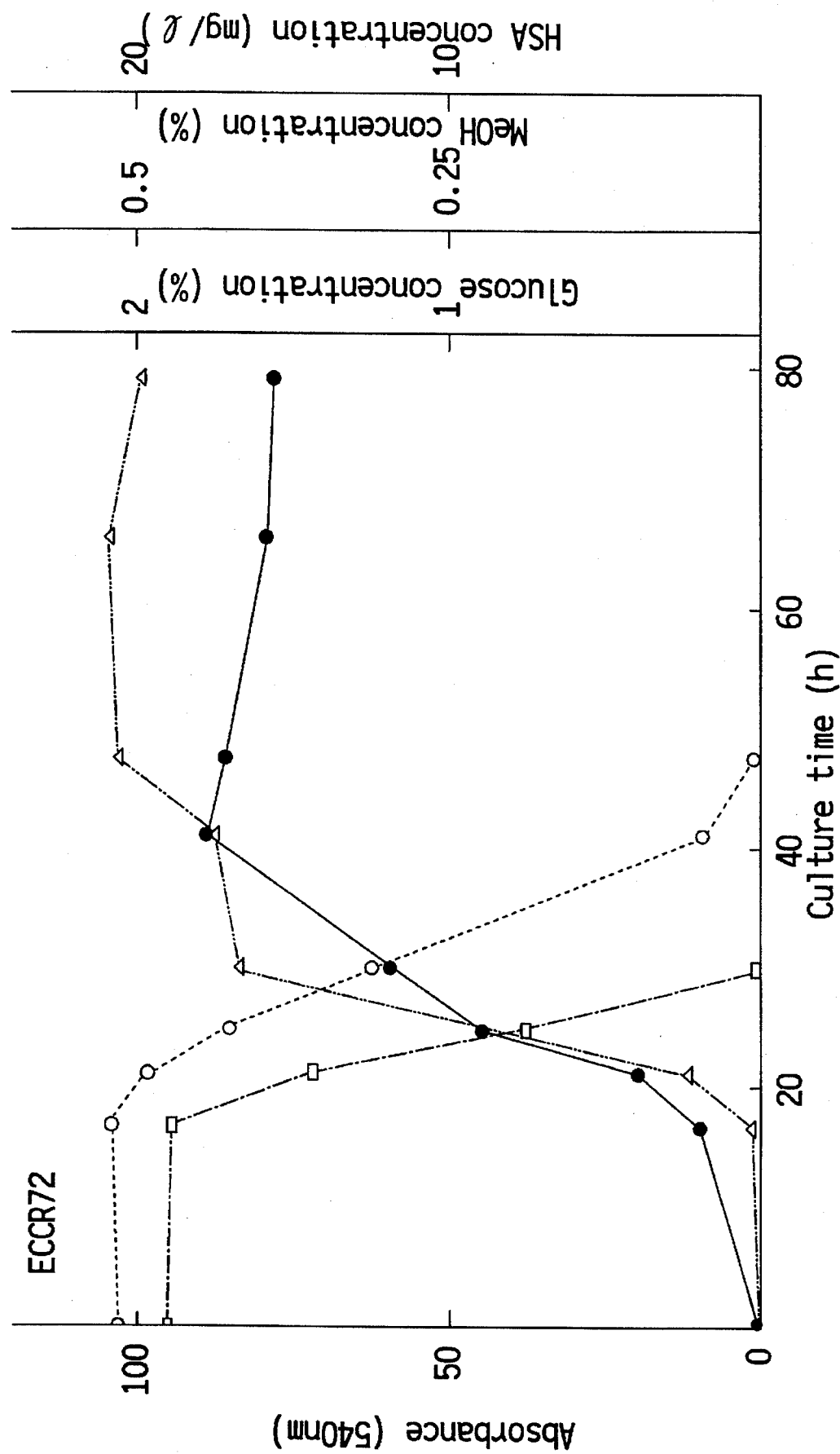

MUTANT STRAIN OF *PICHIA PASTORIS* WHICH UTILIZES METHANOL IN THE PRESENCE OF GLUCOSE

TECHNICAL FIELD OF THE INVENTION

The present invention relates to a novel mutant strain and a method for producing a heterologous protein by culturing the strain.

BACKGROUND OF THE INVENTION

A methylotrophic strain can grow with methanol as a carbon and energy source. This is attributable to the fact that it has a gene encoding alcohol oxydase (EC1. 1. 3. B, hereinafter also referred to as AOX) which is an enzyme catalyzing a first reaction in the metabolism of methanol, namely, oxidation of methanol into formaldehyde.

A methylotrophic strain can metabolize methanol by the action of the AOX it produces even in a medium containing methanol as a sole carbon source and can grow on the metabolite of methanol as a carbon source.

*Pichia pastoris* is one of the methylotrophic yeasts and has two kinds of AOX genes, AOX1 gene and AOX2 gene, each having a promoter, a structural gene and a terminator in their chromosomes. Their structural genes have high homology with each other and code for AOXs having similar specific activities. As regards their promoters, however, they are known to have remarkably different transcription activities (AOX1 promoter>AOX2 promoter) and AOX actually produced is mostly derived from the AOX1 gene [Molecular and Cellular Biology, Vol. 9, 1316 (1989)].

In recent years, methods for producing heterologous proteins by using AOX genes of a Pichia yeast have been studied [Yeast, 5, 167–177 (1989), U.S. Pat. No. 4,929,555, EP-A-344459, EP-A-347928]. A strain comprising a gene encoding a desired heterologous protein inserted in the place of a structural gene at the downstream from an AOX1 promoter having high promoter activity is superior in transcription efficiency, whereas the growth thereof in a medium containing methanol as a carbon source is poor due to a very small amount of produced AOX (which permits methanol utilization) by an AOX2 gene alone having poor expression activity, and an extended culture is necessary for producing a heterologous protein.

It has now been found that the mutation of the AOX2 promoter of the strain results in an enhanced promoter activity to afford an increased production of AOX by the AOX2 gene. Thus, the mutation of the AOX2 promoter has made it possible for the strain to grow well in a medium containing methanol.

Together, however, it has been found that the AOX promoters of the strain are subject to catabolite repression caused by glucose in a medium. That is, the transcription activity of AOX promoters is repressed in the presence of glucose in a medium, thus resulting in failure to express an AOX gene and a heterologous protein gene which are under the control of the above-mentioned promoters. Although the strain synthesizes its constitutive protein and can grow on glucose as a carbon source, it does not produce AOX and heterologous protein. The same applies to a medium containing both methanol and glucose. In this case, it is not until glucose has been completely consumed that AOX promoters begin to act to produce AOX and a heterologous protein.

Alternatively, the aforementioned strain undesirably requires an extended time for producing a heterologous protein, which is unbeneficial for efficient production of a desired heterologous protein.

SUMMARY OF THE INVENTION

Accordingly, an object of the present invention is to solve the aforementioned problems encountered by the conventional production methods and to provide a strain permitting constitutive, efficient expression and production of AOX and a heterologous protein which are inherently inducible.

Another object of the invention is to provide a method for producing a heterologous protein in large amounts in a short time by using this strain.

BRIEF DESCRIPTION OF THE DRAWINGS

FIGS. 2A and 2B show modes of presence of a unit and AOX gene(s) when a cell (starting strain) is carrying two AOX genes, in which FIG. 2A shows direct insertion of the unit into a cell and FIG. 2B shows replacement, in a chromosome, of a structural gene in the AOX gene with a gene encoding a heterologous protein.

FIG. 5 shows the time-course change of cell density (absorbance), concentrations of glucose and methanol and concentration of HSA produced in the medium when ECCR72 strain was cultured in YPDM medium, wherein —●— is absorbance, —○— is glucose, —□— is MeOH, and —△— is HSA.

DETAILED DESCRIPTION OF THE INVENTION

Figure 1:
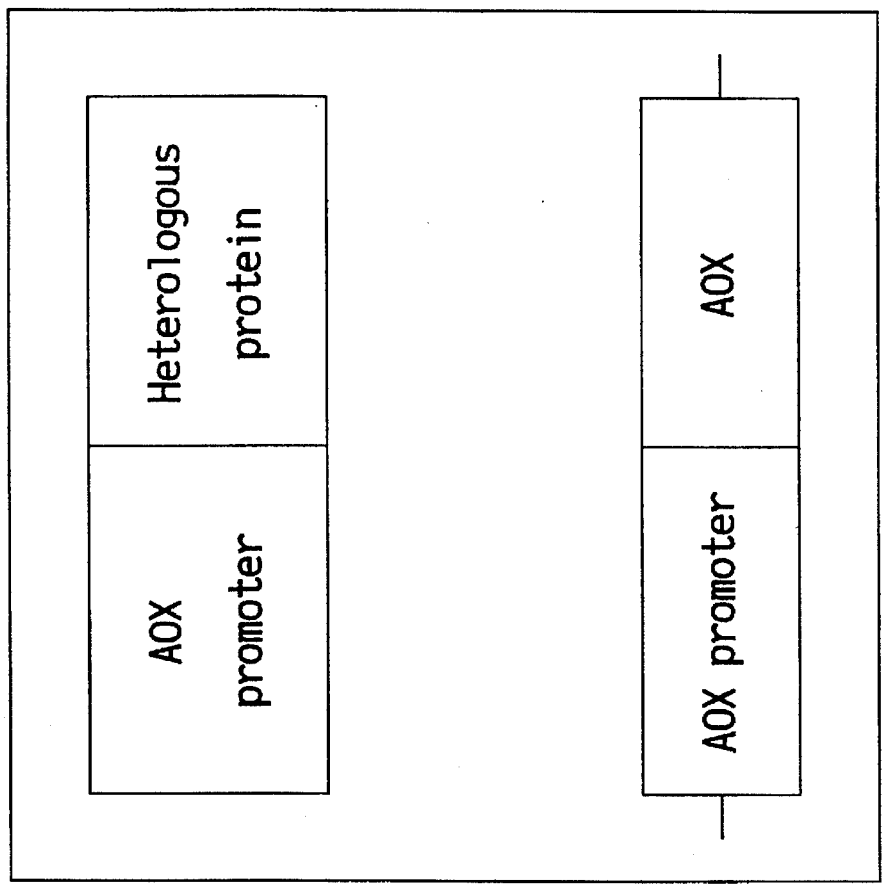
FIG. 1 shows a mode of presence of a unit (which permits expression of a heterologous protein gene under the control of an AOX promoter) and an AOX gene when the unit was directly introduced into a cell (starting strain) carrying one AOX gene.
Figure 1:
Figure 1:
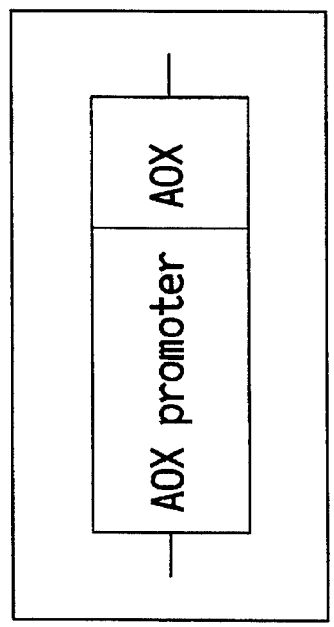

In an effort to afford a desired substance at high yields in a short time, the present inventors have found that a mutant strain which is glucotrophic as well as methylotrophic can be prepared by treating the above-mentioned strain with a mutagen such as ethyl methanesulfonate (hereinafter referred to as EMS).

Namely, the present invention provides a methylotrophic and glucotrophic mutant strain capable of producing a heterologous protein and a method for producing said strain. The present invention also relates to a method for producing a heterologous protein by culturing said mutant strain.

The mutant strain of the present invention is a strain obtained by mutating a strain, which is inherently inducible in the expression of a heterologous protein gene, into a constitutive one.

As used herein, the term "constitutive" means that an expression and production of a protein by the strain can be performed at a certain consistent level without being influenced by culture conditions. In the present invention, the constitutive property of the mutant strain concretely means that the growth of the strain (e.g. cell-constitutive protein), expression of a gene in the strain, production of a protein etc. are not influenced by the presence of glucose in a medium.

As used herein, the term "inducible" means that the expression and production are subject to repression caused by catabolites, metabolites, inducers etc. This is attributable to the fact that a transcription activity of a promoter is under the control of transcription regulatory genes which are controlled by catabolites, metabolites, inducers etc. For example, an AOX promoter is an inducible promoter having the above-mentioned properties, and the transcription activity of said promoter is controlled by glucose.

The mutant strain of the present invention may be any irrespective of how it is obtained, insofar as it is capable of utilizing both methanol and glucose to produce a heterologous protein.

Specifically, a strain obtainable by treating a methylotrophic strain capable of producing a heterologous protein with a mutagen is exemplified.

(1) Methylotrophic Strain Capable of Producing a Heterologous Protein

The starting strain to be treated with a mutagen in the present invention is a methylotrophic strain capable of producing heterologous protein. This methylotrophic strain is subject to catabolite repression caused by glucose. In a medium containing both methanol and glucose, the strain first consumes glucose for its growth without producing a heterologous protein, and upon complete consumption of the glucose, it starts consuming methanol to produce a heterologous protein. Thus, the strain can utilize methanol to produce a heterologous protein, and it is preferably a methylotrophic strain capable of expressing and producing a heterologous protein under the control of an AOX promoter. The strain contains at least a gene which permits expression of a heterologous protein gene under the control of an AOX promoter (hereinafter the gene is also referred to as unit), and preferably contains said unit and a gene to cause expression of an AOX gene under the control of an AOX promoter (hereinafter the gene is also referred to as AOX gene) in one strain. Specific modes of the presence of a unit and an AOX gene in a strain are shown in FIGS. 1 and 2.

The unit may be integrated into a chromosome of a methylotrophic strain by insertion or replacement, or it may be incorporated into a plasmid etc. in a methylotrophic strain cell.

The methylotrophic strain carrying such a unit may be prepared by optional means which is not subject to any particular limitation.

Figure 2A:
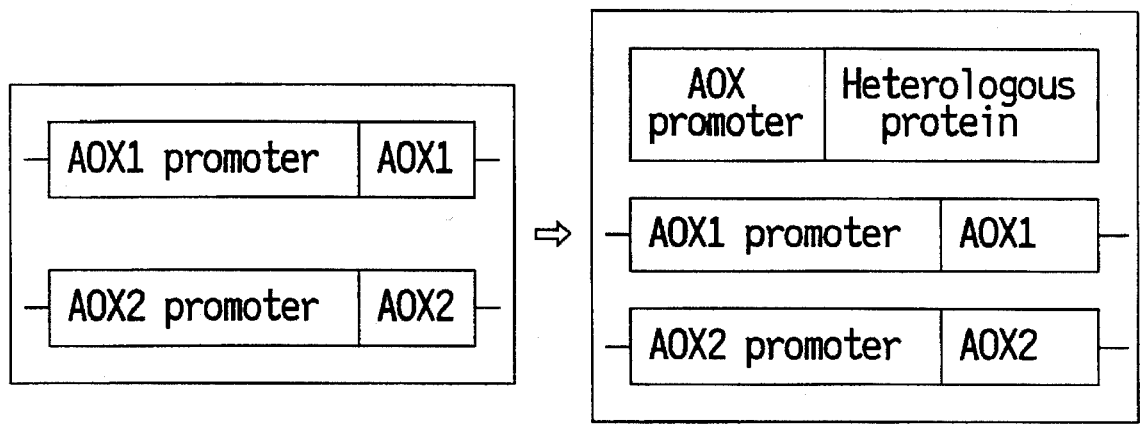
Figure 2B:
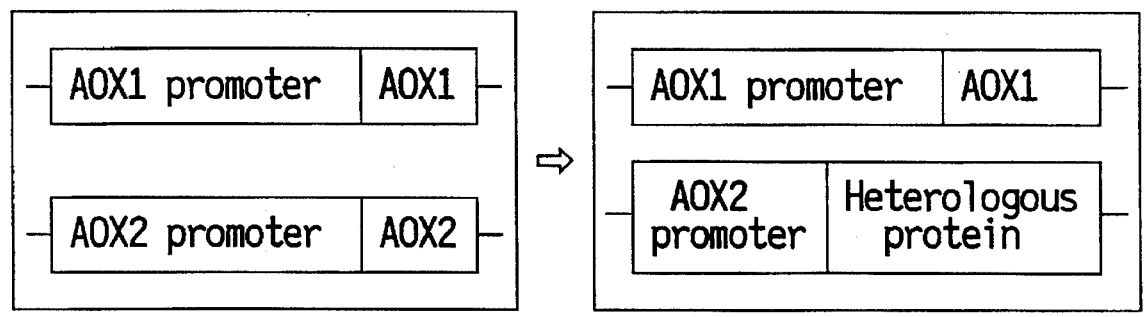
Figure 2B:
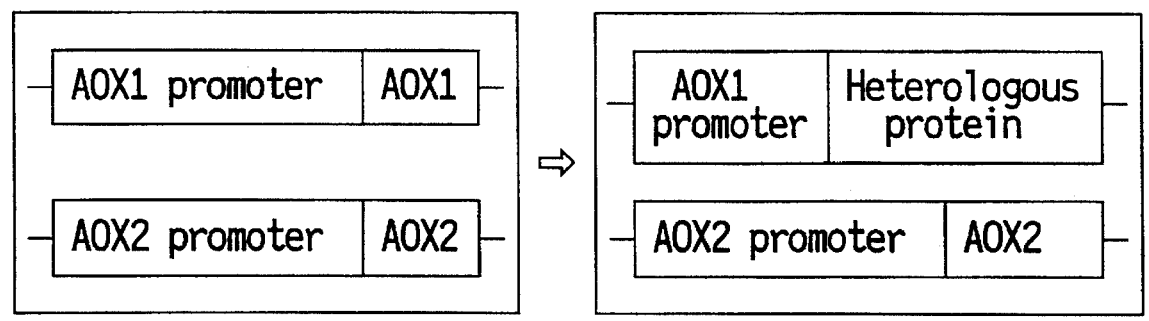

When using a methylotrophic strain carrying one AOX gene, for example, a methylotrophic strain carrying the above-mentioned unit can be prepared by directly introducing the unit, which causes production of a heterologous protein under the control of an AOX promoter, into a cell (FIG. 1). A methylotrophic strain carrying two AOX genes can be prepared likewise by directly introducing a unit into a cell to prepare a strain having two AOX genes and a unit (FIG. 2A). Further, by integrating a gene encoding a heterologous protein into a region downstream from an AOX promoter of one of the AOX genes in a chromosome of a strain such that the heterologous gene is under the control of the promoter, a strain carrying a unit corresponding to the unit as described can be prepared (FIG. 2B).

Alternatively, such strain can be prepared by introducing a plasmid vector or a phage vector carrying said unit and (an) AOX gene(s), into a suitable methylotrophic strain. The preparations mentioned above can be done by steps known per se.

The number of the copy of the unit to be introduced into a methylotrophic strain may be one or more.

Such unit may contain a ribosome binding site, a translation initiation codon, a DNA having a nucleotide sequence encoding a signal peptide, a translation termination codon, a terminator, a selection marker gene, an autonomously replicating sequence and so on.

The AOX promoter in a methylotrophic strain may be a wild type promoter insofar as it shows promoter activity, and may be mutated or modified. Preferably, the promoter is a wild-type AOX promoter with higher promoter activity or an AOX promoter with a promoter activity enhanced by modification or mutation.

In the case of Pichia yeasts, a wild-type AOX1 promoter with higher promoter activity and a mutant AOX2 promoter with a promoter activity enhanced by mutation or modification by a suitable treatment are exemplified.

The said mutant AOX2 promoter can be obtained from a strain improved in methanol utilization, the improvement being achieved by subculturing a strain derived from a Pichia yeast, which carries a wild-type AOX2 promoter on its chromosome and fails to produce AOX with an AOX1 gene, in a medium containing methanol as a sole carbon source such that a mutation is caused. Also, it can be chemically synthesized while referring to the nucleotide sequence of the thus-obtained mutant AOX2 promoter or treating a wild-type AOX2 promoter by a known genetic engineering technique such as a site-directed deletion [Nucl. Acids Res., 11, 1645 (1983)], a site-directed mutagenesis or a restriction enzyme treatment.

Examples of the methylotrophic strain include Pichia yeast (*Pichia pastoris*), yeasts belonging to the genus Hansenula, the genus Candida, the genus Rhodotorula or the genus Sporobolomyces, and bacteria belonging to *Methylomonas methanica*, *Methylophilus methylotrophus*, the genus Methylococcus, the genus Methylosinus, the genus Pseudomonas or the genus Methylobacterium.

Examples of the heterologous protein include human serum albumin, hepatitis B virus antigen, prourokinase, tissue plasminogen activator, various interferons, immunoglobulin and colony stimulating factors.

The heterologous protein gene (structural gene) to be used may be any insofar as it codes for a desired heterologous protein and it may be prepared by any method. The structural gene is preferably inserted into a region downstream from an AOX promoter by a known genetic engineering technique and introduced into a methylotrophic strain. For this end, usable is a transformation method for integration of a structural gene into a chromosome, a method for direct introduction into a methylotrophic strain cell or the like.

Specific examples of the strain as described include GCP101 strain, SHG4105 strain, UHG42-3 strain (EP-A-506040) and so on.

(2) Mutation by Treating With a Mutagen

The mutant strain of the present invention can be obtained by treating a strain mentioned in (1) above in the presence of about 0.1–10% mutagen such as EMS per $10^6$–$10^{10}$ cell/ml of the strain at 5°–37° C. for about 10 minutes to 3 hours.

Then, the obtained mutant strain is cultured in a suitable medium containing methanol [e.g. YPM medium (1% bacto yeast extract, 2% bacto peptone, 1% methanol)] and supplemented with about 0.01–0.1% 2-deoxyglucose, to give the mutant strain of the present invention.

As the mutagen, usable besides EMS are, for example, 2-aminopurine, hydroxylamine, N-methyl-N'-nitro-N-nitrosoguanidine and acridine, which may be used alone or in combination.

(3) Properties of the Obtained Mutant Strain

The mutant strain of the present invention is free of catabolite repression caused by glucose. Accordingly, the mutant strain can be cultured in a medium containing methanol and glucose, not to mention a medium containing methanol as a sole carbon source, and can grow therein as well as produce a heterologous protein.

(4) Production of a Heterologous Protein by Culturing a Mutant Strain

The mutant strain thus obtained is cultured in a suitable, known medium to produce a desired heterologous protein.

The medium contains a carbon source, a nitrogen source, minerals, vitamins, drugs and so on, which are indispensable for the growth of a mutant strain.

To be specific, a medium containing methanol as a sole carbon source or a medium containing methanol and glucose in conjunction can be used.

Examples of the medium when the mutant strain is a yeast include YPDM medium (1% bacto yeast extract, 2% bacto peptone, 2% glucose, 0.5% methanol), YPD medium (1% bacto yeast extract, 2% bacto peptone, 2% glucose), YPG medium (1% bacto yeast extract, 2% bacto peptone, 2% glycerol), YPM medium (1% bacto yeast extract, 2% bacto peptone, 2% methanol), YNB liquid medium containing 0.1–5% methanol (0.7% yeast nitrogen base, manufactured by Difco), YP medium containing 0.01–5% methanol (1% bacto yeast extract, manufactured by Difco, 2% Poly Peptone (manufactured by Daigo Elyosha, Japan) and SMM medium (2% methanol, 0.5% $CH_3COONH_4$ synthetic medium).

Cultivation is usually carried out at a temperature between 15° C. and 45° C., preferably about 20°–40° C. for 1–200 hours, with aeration and/or agitation applied as necessary. The pH of the medium is preferably from 5 to 8.

After culture, the desired heterologous protein accumulated in the culture supernatant or in the mutant strain is extracted and purified by known methods. For example, salting-out, solvent precipitation, dialysis, ultrafiltration, gel electrophoresis, gel filtration chromatography, ion exchange chromatography, reverse phase chromatography, affinity chromatography and so on may be used in combination.

Note that various techniques, reactions and analysis methods to be used in the present invention are known to those of ordinary skill in the art. Also, enzymes, plasmids and so on may be those commercially available.

The present invention is hereinbelow described in more detail by way of an example and a reference example, to which the invention is not limited.

All the enzymes used in the following example and reference example were obtained from commercial supply sources such as Takara Shuzo Kabushiki Kaisha, Japan, unless specifically indicated.

Buffers for enzyme reactions and reaction conditions followed manufacturer's recommendations for each enzyme, unless particularly specified.

Pichia pastoris GTS115 strain, GCP104 strain and plasmid pPGP1 were obtained from Phillips Petroleum.

The ECCR72 strain obtained in Example 1 was deposited at the Institute for Fermentation, Osaka on Dec. 28, 1992 under the deposit number IFO 10612.

REFERENCE EXAMPLE AND EXAMPLE

Figure 3:
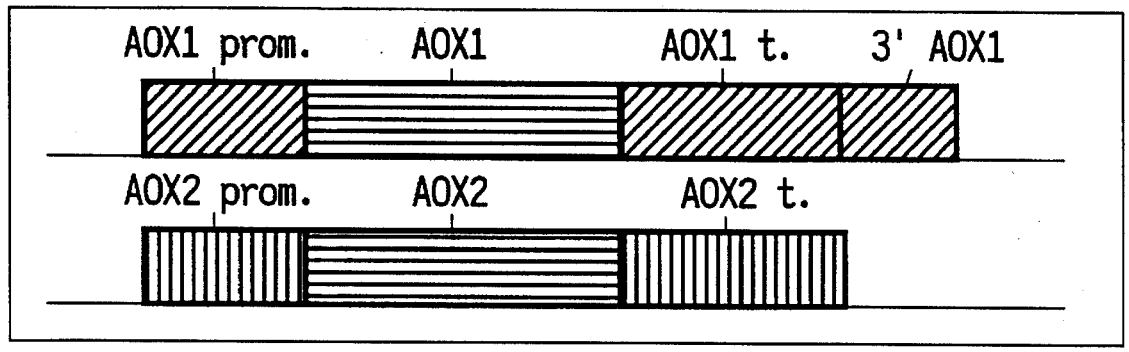
FIG. 3 shows AOX1 and AOX2 gene regions in GTS115 strain and GCP104 strain, and a schematic presentation of the preparation of GCP101 strain, wherein prom. is promoter, t. is terminator and poly is poly A region.
Figure 3:
Figure 3:
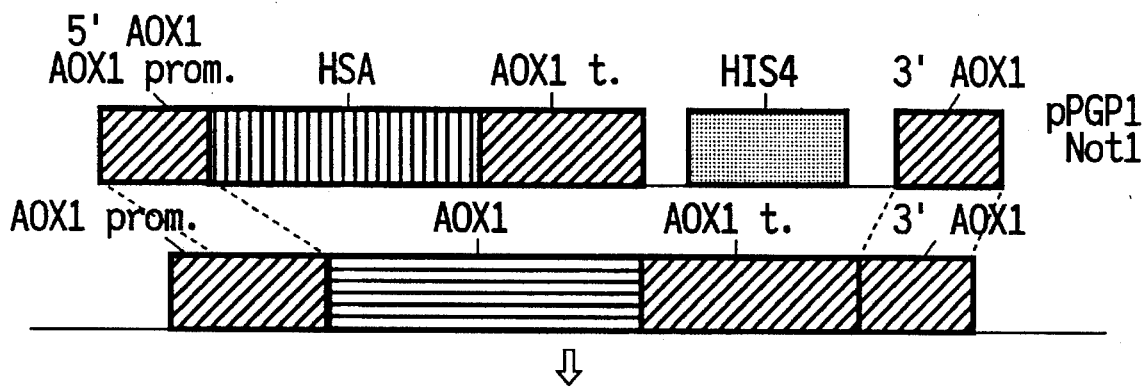
Figure 3:
Figure 3:
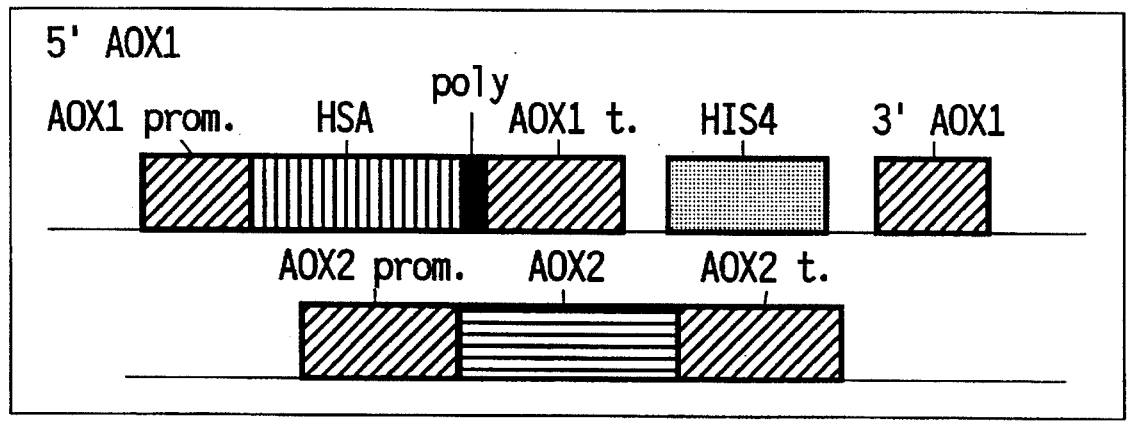
Figure 3:

Reference Example 1 Obtainment of GCP101 Strain (Mut+ Strain) (FIG. 3)

According to the method as described in EP-A-344459, a fragment was obtained by cleaving plasmid pPGP1, which has a transcription unit permitting HSA expression under the control of an AOX1 promoter, with a restriction enzyme NotI and the obtained fragment was introduced into *Pichia pastoris* GTS115 to replace the AOX1 gene region thereof, whereby GCP104 strain (AOX1-deleted strain) was obtained. This strain lacked a structural gene of AOX1, leaving production of AOX which permits methanol utilization to an AOX2 gene alone having a poor expression efficiency. Therefore, its growth potency in a medium containing methanol as a sole carbon source was poor (Mut- strain).

The GCP104 strain was inoculated into 3 ml of YPD medium (1% bacto yeast extract, 2% bacto peptone, 2% glucose) and 24 hours later, it was inoculated into 50 ml of YPD medium at a concentration with an initial $OD_{540}$ of 1. After culture at 30° C. for 3 days, it was inoculated into 50 ml of YPM medium (1% bacto yeast extract, 2% bacto peptone, 2% methanol) at a concentration with an initial $OD_{540}$ of 1. Then, using YPM medium, a subculture in a similar manner was repeated every 3 days. At every subculture, cells were diluted with sterilized water to a concentration of $10^7$ cell/plate and spread on a 2% methanol-YNB w/o a.a. plate (0.7% yeast nitrogen base without amino acid, 2% methanol, 1.5% gelatin). The cells were incubated at 30° C. for 5 days and the presence of colony was assessed. As a result, 20 colonies were obtained from a 2% methanol-YNB w/o a.a. plate spread upon 12 days subculture.

Since methanol was the sole carbon source in this plate, a Mut- strain with poor methanol utilization could hardly grow. Therefore, the colonies formed on this plate were those of a mutant Mut+ strain with improved methanol utilization. An improvement in methanol utilization was attained as a result of mutation of an AOX2 promoter, which brought an enhanced promoter activity permitting production of AOX which is derived from an AOX2 structural gene. One of the colonies was suitably diluted with sterilized water, spread on a 2% methanol-YNB w/o a.a. plate, and isolated into single colonies. One of them was named GCP101.

Example 1

Mutation With a Mutagen and Production of a Heterologous Protein by Culturing the Obtained Mutant Strain (1) Mutation The GCP101 strain as obtained in Reference Example 1 was cultured in YPD medium and EMS was added to the medium at a concentration of 2.9% per $2\times10^8$ cell/ml, followed by incubation at 30° C. for 1 hour. Then, a 2-deoxyglucose resistant strain (which is a mutant strain) was obtained using YPM medium (1% yeast extract, 2% bacto peptone, 1% methanol) supplemented with 0.02% 2-deoxyglucose.

The mutation frequency of the 2-deoxyglucose resistant strain by EMS was $1.4\times10^{-4}$–$3.3\times10^{-4}$ which was about 100 times higher than the frequency of $2\times10^{-7}$–$2\times10^{-6}$ without EMS treatment.

(2) Subculture

The mutant strain obtained in the above was subcultured in YPM medium (1% yeast extract, 2% bacto peptone, 1% methanol) supplemented with 0.02% 2-deoxyglucose and ECCR72 strain (which is a 2-deoxyglucose resistant strain) was selected and isolated.

(3) Main Culture

The cell suspension of the aforementioned ECCR72 strain, which had been cultured overnight in YPD medium (1% yeast extract, 2% bacto peptone, 2% glucose), was inoculated into 50 ml of YPDM medium (1% yeast extract, 2% bacto peptone, 2% glucose, 0.5% methanol) at a concentration of 1% and subjected to shake culture at 30° C. in a 300 ml Erlenmeyer flask equipped with baffles. As a reference strain, a starting strain GCP101 was cultured in the same manner and cell density (absorbance at 540 nm), glucose concentration, methanol concentration and the concentration of HSA produced were measured with time for comparison.

(4) Results

Figure 4:
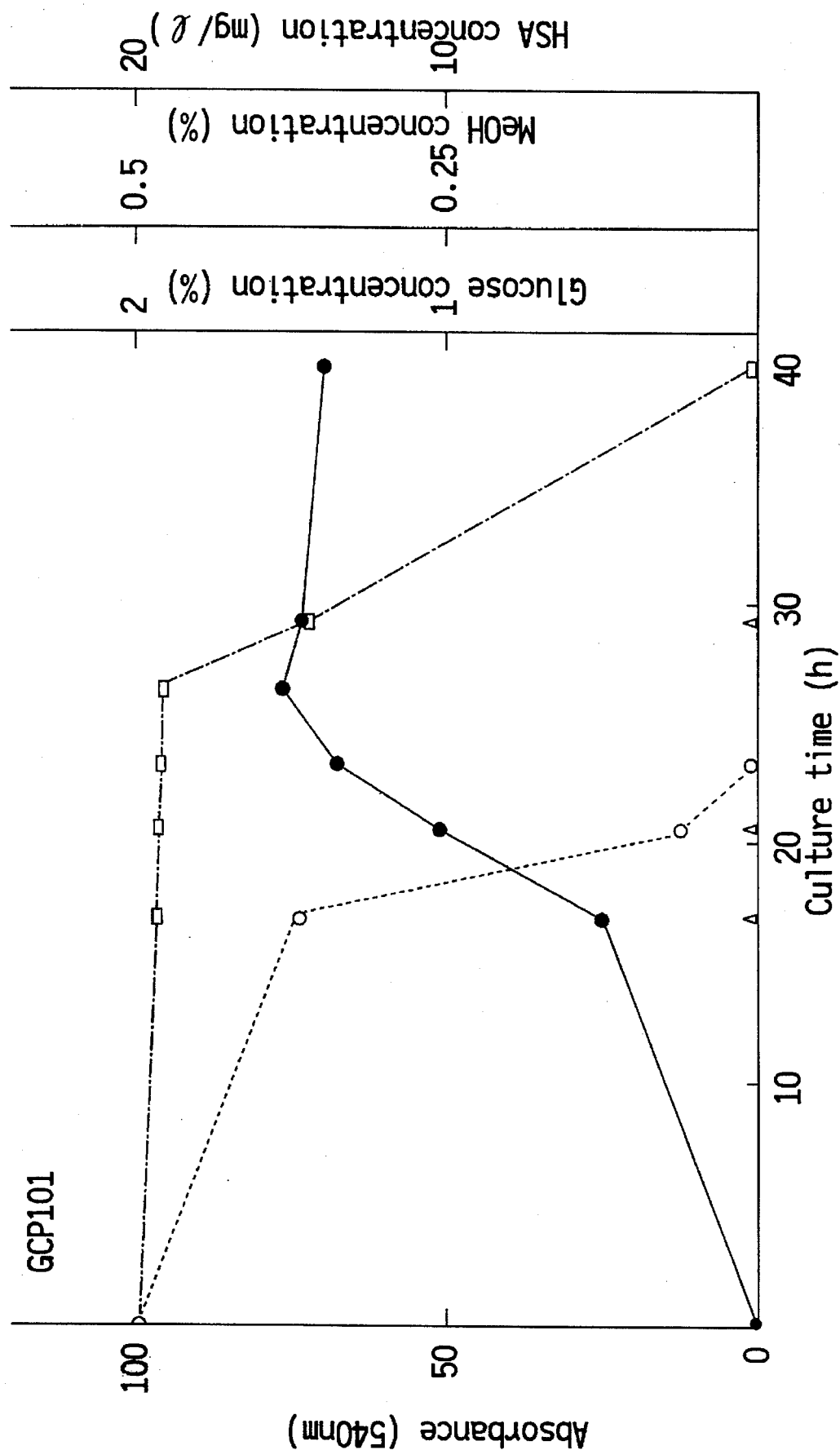
FIG. 4 shows the time-course change of cell density (absorbance), concentrations of glucose and methanol and concentration of HSA produced in the medium when GCP101 strain was cultured in YPDM medium, wherein —●— is absorbance, —○— is glucose, —□— is MeOH, and —△— is HSA.

A glucose catabolite repression where glucose consumption precedes methanol consumption was observed and HSA was not produced within the experiment period in GCP101 strain (FIG. 4).

On the other hand, ECCR72 strain consumed glucose and methanol simultaneously. As the methanol consumption proceeded, HSA was confirmed to be secreted in the medium (FIG. 5).

The mutant strain of the present invention can be grown in a medium containing both methanol and glucose, with the effect that the growth of the strain and production of a heterologous protein proceed at the same time. Accordingly, a heterologous protein can be produced in a large amount in a short time.

What is claimed is:

1. A mutant *Pichia pastoris* strain having a gene encoding a heterologous protein, wherein said *Pichia pastoris* strain utilizes methanol in the presence of glucose to produce said heterologous protein.

2. The mutant strain of claim 1, which is obtained by treating a methylotrophic *Pichia pastoris* strain which produces the heterologous protein with a mutagen.

3. The mutant strain of claim 1 or claim 2, wherein the heterologous protein is selected from the group consisting of human serum albumin, hepatitis B virus, prourokinase, tissue plasminogen activator, interferon, immunoglobulin and colony stimulating factor.

4. The mutant strain of claim 2, wherein the methylotrophic strain produces the heterologous protein under the control of an AOX promoter.

5. The mutant strain of claim 2, wherein the methylotrophic strain comprises a gene which expresses the protein gene under the control of an AOX promoter and an AOX gene under the control of an AOX promoter.

6. The mutant strain of claim 1, wherein said gene encoding said heterologous protein is present in a chromosome.

7. The mutant strain of claim 2, wherein the mutagen comprises at least one of ethyl methanesulfonate, 2-aminopurine, hydroxylamine, N-methyl-N'-nitro-N-nitrosoguanidine or acridine.

8. A method for producing a heterologous protein, comprising culturing the mutant strain of claim 1 or claim 2 in the presence of methanol and glucose to produce the heterologous protein.

9. The method for producing a heterologous protein according to claim 8, wherein the heterologous protein is selected from the group consisting of human serum albumin, hepatitis B virus, prourokinase, tissue plasminogen activator, interferon, immunoglobulin and colony stimulating factor.

10. The mutant strain of claim 1, comprising an AOX promoter not subject to repression by glucose.

* * * * *